United States Patent [19]

Pace

[11] 4,225,410

[45] Sep. 30, 1980

[54] INTEGRATED ARRAY OF ELECTROCHEMICAL SENSORS

[75] Inventor: Salvatore J. Pace, Yorktown Heights, N.Y.

[73] Assignee: Technicon Instruments Corporation, Tarrytown, N.Y.

[21] Appl. No.: 966,171

[22] Filed: Dec. 4, 1978

[51] Int. Cl.² ............... G01N 27/30; G01N 31/14
[52] U.S. Cl. .................. 204/195 R; 204/1 T; 204/195 B; 422/98; 435/4; 435/817
[58] Field of Search ............ 364/416, 497; 195/127; 204/195 R, 195 B, 1 E; 422/90, 98; 128/2 E, 2 G, 635

[56] References Cited

U.S. PATENT DOCUMENTS

| | | | |
|---|---|---|---|
| 3,838,034 | 9/1974 | Groves | 204/195 B |
| 3,890,201 | 6/1975 | Cady | 195/127 |
| 4,020,830 | 5/1977 | Johnson et al. | 128/2 E |
| 4,072,578 | 2/1978 | Cady et al. | 195/127 |

OTHER PUBLICATIONS

Richard A. Durst, "Ion-Selective Electrodes", NBS Special Pub. 314, pp. 113, 114, (1969).

*Primary Examiner*—G. L. Kaplan
*Attorney, Agent, or Firm*—S. P. Tedesco

[57] ABSTRACT

A disposable integrated miniaturized array of chemical sensors for analyzing concurrently a number of analytes in a fluid sample is described. Each sensor is a complete electrochemical cell consisting of its own individual reference and indicator electrodes and is selective with respect to a particular analyte in the sample.

Where required, a sensor can be individually calibrated, such that each analysis can be read directly.

5 Claims, 21 Drawing Figures

INTEGRATED ARRAY OF ELECTROCHEMICAL SENSORS

FIELD OF THE INVENTION

This invention relates to an article of manufacture and, more particularly, to an integrated array of chemical sensors for rapidly performing concurrent multiple analyses of analytes in a fluid sample.

BACKGROUND OF THE INVENTION AND DISCUSSION OF THE PRIOR ART

In the past, multiple chemical assays have been performed on biological fluid samples such as whole blood, plasma, or serum. Generally, such testing has been carried out by continuous-flow systems such as those shown in the U.S. Patents to: L. T. Skeggs, U.S. Pat. No. 2,797,149, issued June 25, 1957; L. T. Skeggs-E. C. Whitehead-W. J. Smythe-J. Isreeli-M. H. Pelavin, U.S. Pat. No. 3,241,432, issued Mar. 22, 1966; W. J. Smythe-M. H. Shamos, U.S. Pat. No. 3,479,141, issued Nov. 18, 1969; and M. H. Shamos-W. J. Smythe, U.S. Pat. No. 3,518,009, issued June 30, 1970; all assigned to a common assignee.

Also, chemical testing of ionic analytes has been performed in an automated fashion using thin films of material, such as shown in the U.S. Pat. No. 4,053,381, issued Oct. 11, 1977 to Hamblen et al.

In order to perform blood testing, however, a great number and variety of tests have to be made. This will naturally require many electrochemical cells of different structures and chemistries. There is little savings in time, sample size and monies in performing each test separately. Rapid and cost-effective methods require a simultaneous analysis of all the analytes in a fluid sample. Emphasis must also be directed to reduction of the sample size; preferably to a few drops or less of blood to minimize demands on the subject, e.g., in the case of infants.

A device that suggests an integrated circuit approach for the testing of a variety of blood analytes in a sample is shown in U.S. Pat. No. 4,020,830 issued to C. C. Johnson et al on May 3, 1977. This device features an integrated array of field effect transistors (FETs), each designed as a discrete sensor. While this is a valid approach to the automated testing of blood samples, certain shortcomings are inherent in this technique.

(a) Only ion-selective FETs have been successfully and reliably demonstrated. When designed to measure non-ionic analytes, the FET structure becomes very complex, because an additional electrochemical cell must be placed at the gate electrode of the FET to influence the measured drain current. This measurement, however, requires a constant current source in addition to the cell FET and external reference electrode.

(b) Instability in any complement will naturally cause fluctuations in the drain current, and, hence, errors in the measurement of the analyte. In addition, the proposed enzyme and immuno FETs have polymer layers, where concurrent processes such as adsorption and ionic double layer capacitance changes can effect the electric field at the gate of the FETs. Extraneous electric fields are also produced at the fringes of the gate area. These effects will likewise cause errors in the analysis of the analytes.

(c) The need for an external reference electrode when measuring non-ionic analytes complicates the integration of a FET array.

(d) FETs will only detect a charged molecule, i.e., an ion. Non-charged analytes do not influence the gate voltage in an interference-free manner. Hence, analytes which can be successfully analyzed are limited.

However, the semiconductor fabrication technology is so advanced that very precise miniature devices can be easily and cheaply manufactured. Furthermore, precedence has been established for superior stability, reproducibility and sensitivity. Hence, this invention seeks to combine the best attributes of two technologies (electrochemistry and semiconductors) to achieve integration of sensors without the drawbacks and limitations of the FET approach.

The present invention contemplates the structure and fabrication of a micro-miniaturized, multi-functional, electrochemical, integrated circuit chip or array of improved electrochemical sensors. This circuit chip requires a minimal sample volume to effect the simultaneous analysis of a plurality of analytes in on-site fashion. In addition, immediate analysis will be affordable by use of this circuit chip which can be easily analyzed, or "read out" by a small, hand-held analyzer or computer at the scene of an emergency or at a patient's bedside. As the circuit chip is relatively inexpensive, it may be disposable. Since the sample can be whole blood, sample handling by the user is minimized. Also, as a plurality of analytes can be simultaneously analyzed, requiring only a minimum volume of blood sample, e.g., one drop or less of fluid, the advantages to be gained by the invention are considerable.

SUMMARY OF THE INVENTION

This invention relates to a micro-miniaturized, multi-functional, electro-chemical, integrated circuit chip of electro-chemical sensors for analyzing concurrently a plurality of analytes in a minimal sample volume. The circuit chip comprises a substrate supporting a plurality of individual sensors arranged in a dense but discrete relationship to form an integrated array. Unlike integrated sensor arrays of the prior art, which provide a single common reference electrode, the present invention appreciates that a more reliable analysis results when each electro-chemical sensor has its own reference electrode. Normally, it would be expected that the use of separate reference electrodes for each sensor is an unnecessary duplication of components. The present invention, however, achieves this result while providing a more compact chip, which is of a relatively simple fabrication.

The circuit chips may be a combination of any one or more of three types of electro-chemical cells: (a) a current measuring cell; (b) a potential measuring cell; or (c) a kinetic rate measuring cell. Some of the electro-chemical sensors will be ion-selective and adapted to measure ions, such as Na+ or K+, potentiometrically. Other sensors may be adapted to measure a redox reaction for the detection of glucose, LDH, etc., by amperometric/voltammetric methods.

In one embodiment of the invention, a small, hand-held computer is used to analyze, or "read out", and display the measurements of each of a plurality of analytes in the fluid sample.

While it has been suggested in the prior art to fabricate integrated circuits using semiconductor techniques, as illustrated by the prior-mentioned U.S. Pat. No.

3,020,830, it is believed to be the first time an integrated circuit chip of this kind, consisting of various conventional-type electro-chemical sensors has been so constructed. In addition, the invention teaches improvements in construction, performance, reliability and convenience for these sensing elements.

Each electro-chemical sensor is selective with respect to only one analyte. For example, such selectivity is achieved by providing each sensor with a first porous medium or gel layer containing an immobilized enzyme, specific for only one analyte in the sample. This first porous layer is combined, in some cases, with a second porous filtering layer to selectively screen the fluid sample for a particular analyte. In other cases, the first porous layer functions as a filter to extract the desired analyte from the fluid sample. The first porous layer may also contain a substance to extract the particular analyte and/or make the analyte more soluble in the porous medium, such that the analyte will prefer the porous medium to that of the fluid sample.

A barrier or encapsulating layer is provided for the circuit chip to preserve its shelf-life and to protect against enviornmental or external contamination. In one embodiment, the encapsulating layer can comprise a tear-away, impermeable or mantle. In another embodiment, the barrier layer can comprise a semi-permeable filter layer for preventing contamination and for removing high molecular weight molecules or other particles that may interfere with the chemical analyses of the fluid sample, e.g., red cells in whole blood.

Electrical isolation is accomplished by designing each electro-chemical sensor in the array to have its own specific reference electrode and by electrically isolating the electro-chemical sensor.

The integrated chip can be typically fabricated, as follows:

(a) a substrate is formed by press-forming powdered alumina with appropriate thru-holes and imprints for the electro-chemical circuit; the pressed alumina powder is then fired;

(b) the thru-holes are then filled with conductive material, e.g., pyrolytic carbon;

(c) on the back-side of the substrate, a wiring pattern is deposited using conventional photoresist etching techniques;

(d) on the front-side of the substrate, a pattern of sensor wells are formed by conventional photoresist etching techniques;

(e) with a series of masks, the appropriate layers for each sensor are built up. These layers may comprise polymers or gels including appropriate reagents, i.e., enzymes, and other appropriate substances;

(f) the entire chip is then protected by a coating of epoxy or thermoplastic, with the exception of the sample contact area of the sensors;

(g) a protective barrier is then placed over the sensors.

Generally speaking, the circuit chip of this invention features the following advantages over the prior art:

(a) The circuit chip is intended as a dispoable device, and, therfore, does not suffer from "prior sample memory" problems associated with prior art electro-chemical sensors.

(b) Where required, the electro-chemical sensors include a self-contained calibrating solution to stabilize its particular chemical activity. The calibrating solution may contain a known quantity of analyte and may be impregnated in one of the porous layers of the electro-chemical sensor, which is adapted to minimize capacitive and impedance effects, and eliminates the need of calibrating each test in every sample. For example, in the measurement of potassium, two identical potassium sensing electrodes are incorporated in a single sensor structure and used in a differential mode in a way that external reference electrodes are not required. The layer of the sensor contacting the sample and associated with the sample sensing electrode contains a low concentration of potassium ion (e.g., 1.0 mEq./L.). The layer associated with the other electrode, which is not in contact with the sample, contains a high concentration of potassium ion (e.g., 5.0 mEq./L.). The difference in potassium ion concentration allows calibration of the sensor for sensitivity prior to sample introduction while the differential EMF measurement procedure minimizes signal drift during sample measurement.

In a sensor for the measurement of BUN, as another example, appropriate layers are similarly impregnated with high and low concentrations of $NH_4+$. Additional $NH_4+$ generated by the ureasegel layer results in a change in the differential signal. The self-calibrating sensors also provide ease of fabrication of the circuit chip by reducing the manufacturing tolerances required for the gel layers and electrode structures, because electrodes realistically can never be perfectly matched.

(c) The self-contained integrated structure of electro-chemical sensors, each including its own reference electrode, disposed and interconnected on a common substrate eliminates effects common to other multiple-sensor arrangements, such as liquid junction effects, electrolyte streaming effects and electro-kinetic phenomena. In addition such structure is more compact and easily fabricated.

(d) The barrier layer or encapsulation ensures that the circuit chip can have an extended shelf-life by preventing environmental and external contamination.

(e) Signal-to-noise characteristics are improved, as noise sources are eliminated.

(f) Chemical noise is minimized by confining substances to polymer or gel layers.

(g) Thermal and mass transport gradients are minimized by the commonality of substrates, construction materials, and the miniaturization of the sensing elements.

(h) Each circuit chip is made to interface with a small, hand-held computer, by means of snap-in connections, thus providing on site analyzing convenience and portability.

(i) Sensors for measuring enzyme analytes feature a new method of analysis and a new sensor construction based upon this new analyzing technique, in which:

(1) electrically generating a reactant of said enzyme reaction to establish a steady state condition for the reaction; and (2) electrically monitoring the enzyme reaction to control the generation of the reactant and establish the steady state condition.

The method and apparatus also features: controlling the concentration of a reactant of the enzyme reaction in accordance with the quantity of enzyme in the sample, wherein a steady state condition is rapidly achieved, and then measuring the reaction rate from the steady state condition to determine the activity of the enzyme.

The new sensor construction capable of performing this new technique includes: a generating electrode, a monitoring electrode and a reaction medium disposed therebetween. The steady state is achieved as a result of the rate of reagent formation and rate of depletion by the enzyme reaction.

OBJECTS OF THE INVENTION

It is an object of this invention to provide an improved article of manufacture and apparatus for analyzing a fluid sample;

It is another object of the invention to provide a new article of manufacture and apparatus for the testing of blood analytes, the article of manufacture comprising a disposable integrated circuit chip having an array of electro-chemical sensors;

It is a further object of this invention to provide an article of manufacture and apparatus for simultaneously analyzing a number of analytes in a fluid sample;

It is still another object of the invention to analyze a small quantity of a fluid sample by concurrently contacting all the sensor sites of an integrated multi-functional electro-chemical circuit with the fluid sample;

It is yet a further object of this invention to provide an improved article of manufacture and apparatus for testing blood which features portability, convenience and extremely low cost.

These and other objects of this invention will become more apparent and will be more easily understood with reference to the following detailed description considered in conjunction with the accompanying drawings, in which:

BRIEF DESCRIPTION OF THE DRAWINGS

FIGS. 7a through 7d are further enlarged cross-sectional views of the typical sensors illustrated in FIG. 5;

FIG. 10 is a schematic diagram for the analyzer depicted in FIGS. 3 and 3a;

DETAILED DESCRIPTION

Generally speaking, the invention is for an article of manufacture and an apparatus for analyzing fluid samples containing a number of analytes.

While the invention is primarily directed and described with reference to blood analyses, it should be understood that a great variety of fluid samples can be analyzed by modifying the sensor chemistries.

Figures 1, 1A:
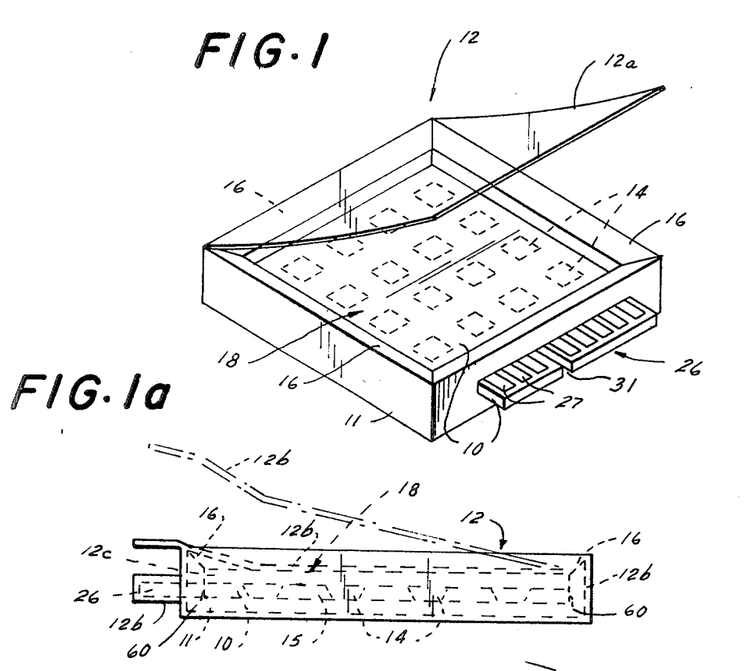
FIG. 1 is a perspective view of the integrate substrate supported chip of this invention shown with an encapsulating layer being removed therefrom.
FIG. 1a is a side view of an alternate encapsulating embodiment to that depicted in FIG. 1.
Figure 2:
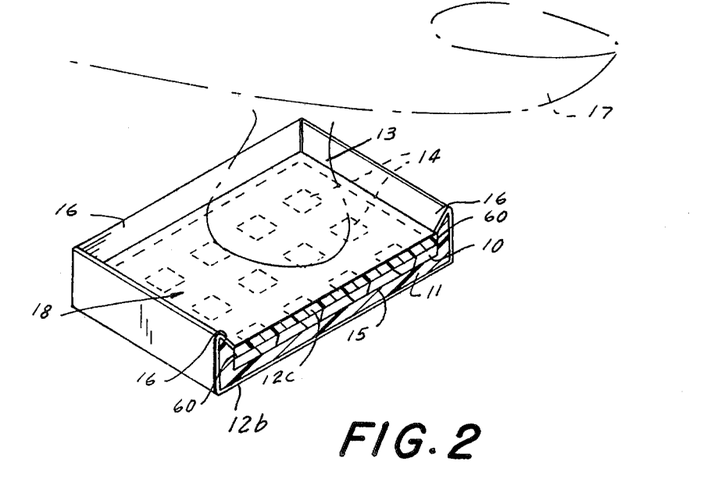
FIG. 2 is a cut-away perspective view of the substrate supported chip of FIG. 1 being deposited with a drop of blood.

Referring to FIGS. 1 and 1a, a circuit chip 10 for analyzing a fluid sample is shown in an enlarged view. The chip 10 is disposed within a hand-held tray support 11. The chip 10 and tray support 11 are both covered by an encapsulating barrier 12 that can either be in the form of a peel-off layer 12a of FIG. 1, or a severable encapsulation envelope 12b of FIG. 1a. The barrier layer 12 may also take the form of a built-in semi-impermeable layer or membrane 12c of FIGS. 1a and 2. The semi-impermeable membrane 12c may also act as a filter, for removing high molecular weight molecules or particles, such as red blood cells. The barrier, regardless of structure, excludes contaminants from chip 10, and thus preserves its reliability and shelf-life. The circuit chip 10 is composed of an array or plurality of spaced-apart sensors 14, which may be planar shaped or designed as miniature cups or wells to receive a drop of blood 13 deposited on the chip 10, as illustrated in FIG. 2. Each sensor 14 is designed and constructed to be specific to a particular analyte in the fluid blood sample 13. This is generally achieved by including within each sensor 14, an enzyme or catalyst that initiates a characteristic reaction. The particular chemistries, reagents, materials, and constructions for each sensor 14 is described in more detail hereinafter.

The hand-held support 11 for the chip 10 comprises a flat base surface 15 and vertically tapered side walls 16 extending from surface 15 for supporting the chip 10 and directing fluid sample 13 into wetting contact with chip 10 and sensors 14. The side walls 16 may be coated with hydrophobic material and serve as a sample confining structure. These side walls 16 define a perimeter of the chip circuit and the outer boundaries of liquid-/chip contact.

Obviously, other designs are achievable within the objectives set forth above, such as, for example, a circular retaining well to replace the square-shaped well defined by walls 16, or a planar boundary wall flush with the surface of the chip (not shown).

The tray support 11 and chip 10 are designed to hold a small volume of sample fluid, i.e., one drop or less. Thus, a finger 17 can be placed directly over the chip 10 and pricked so as to dispense a drop of blood 13 directly onto the chip, as illustrated in FIG. 2. The blood drop 13 spreads over the entire chip 10, to simultaneously wet all sensor sites 14. Because chip 10 is miniaturized, a minimal amount of blood sample will coat the entire sensor surface 18.

Figure 5:
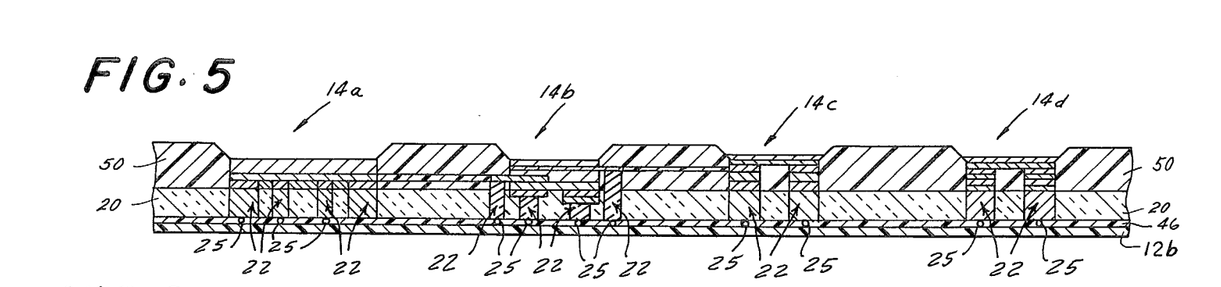
FIG. 5 is a further enlarged cross-sectional view taken along lines 5—5 of a typical row of sensors of the array of sensors shown in FIG. 4.
Figure 7A:
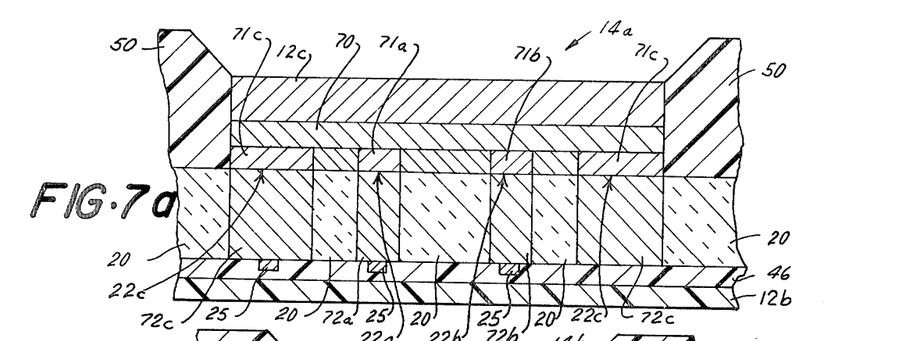
FIG. 7a shows a typical current measuring cell with immobilized enzyme in a gel layer for potassium ion measurement.

Each electro-chemical sensor 14 has a different number of electrodes 22 (FIGS. 5, 8 and 8a) depending upon whether its chemical reaction is measureable as a kinetic rate, a current change or a potential change. The electrodes 22 of each sensor 14 are deposited upon a common substrate 20 of the chip 10, as shown in FIGS. 7a–7d, 8 and 8a, so as to provide a compact and easily fabricated structure. An interconnection circuit 24 is deposited on the opposite side of the common substrate 20 to which all the electrodes 22 are electrically connected, as illustrated in FIGS. 8 and 8a. The use of two surfaces of a common substrate 20 for all the electrodes 22 of each sensor 14 and the signal receiving wires 25 of circuit 24 (FIG. 8a) provide a self-contained, integrated array of sensors 14 unique to chip constructions of this type.

Figure 4:
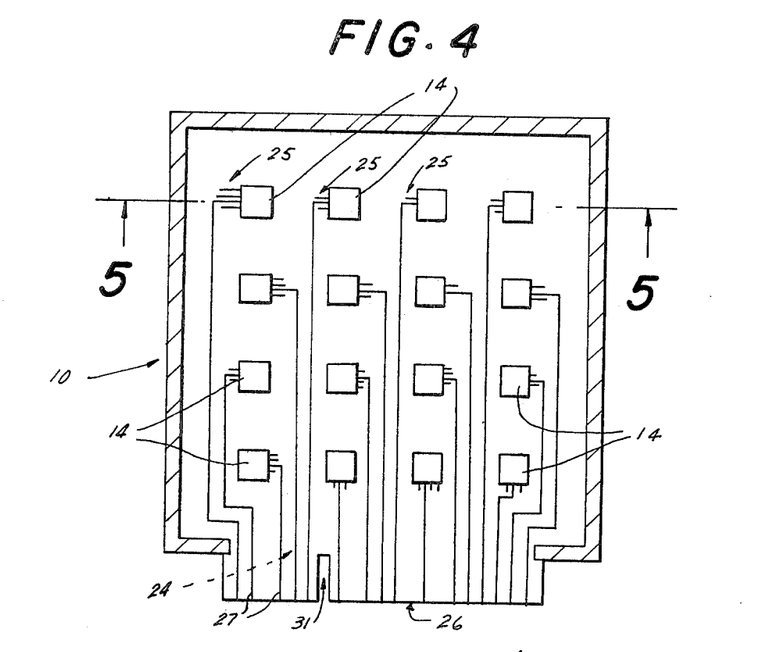
FIG. 4 is a schematic, enlarged plan view of the sensor array on the typical chip of FIG. 1.
Figure 6:
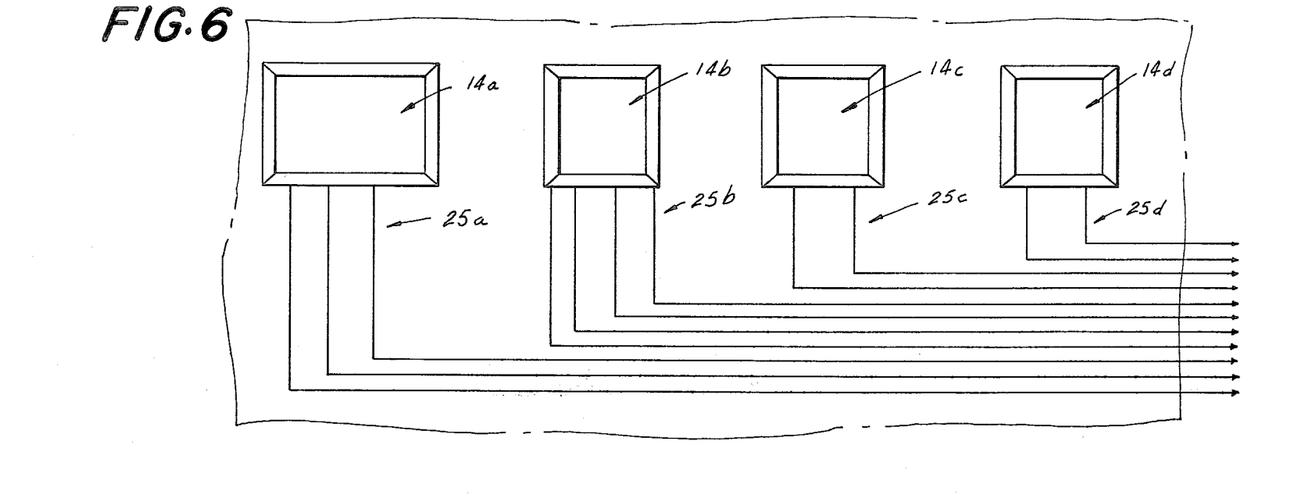
FIG. 6 is an enlarged partial schematic wiring diagram for the typical row of sensors depicted in FIG. 5.

FIG. 4 shows a greatly enlarged schematic plan view of a chip 10 having a typical sensor array. Sixteen sensor sites 14 are depicted, by way of illustration. Each sensor 14 may be symmetrically spaced-apart from the other sensors 14, but this symmetry is not of a functional necessity. Each sensor 14 has a group of electrical interconnectors 25 (FIGS. 4 and 4a) forming part of the interconnection circuit 24. The number of interconnections 25a, 25b, 25c, 25d, etc. for each sensor 14 in a typical sensor row, as shown in FIG. 6, depends upon the type of sensor 14a, 14b, 14c, and 14d, (FIGS. 5 and 6), respectively, being interconnected, as will be described in more detail hereinafter.

The interconnectors 25 each terminate in an electrical connection 27 projecting from the end 26 of chip 10 (FIGS. 1, 3 and 4), which is adapted to mate with a snap-in electrical connector 28 disposed in slot 29 of an analyzing device 30. The connection 27 of chip 10 overhangs the tray 11, as illustrated, and includes a slot 31 for keying into connector 28 of analyzer 30.

The analyzing device 30 (FIGS. 3 and 3a) receives the electrical inputs from each sensor 14 on chip 10 via the snap-in connector 28. Analyzing device 30 may be a hand-held computer, with a keyboard 32 and a display 33. A print-out 34 may also be provided, as shown. Certain keys 35 of keyboard 32, when depressed, interrogate a particular sensor 14 of chip 10. Other keys 35 are adapted to initiate a programmed sequence, such as a test grouping, system calibration, sensor calibration, etc. The analysis of the blood sample 13 for a particular analyte is initiated by depression of a selected key 35 and the result is displayed in display window 33. The signal processing by the analysis device 30 is explained hereinafter with reference to FIGS. 9, 10, and 10a.

Referring to FIG. 8, a perspective cutaway view of a typical sensor site is shown. First, substrate 20 is press-formed from powdered alumina. The appropriate thru-holes 48 for each sensor site 14 are defined in substrate 20. Horizontal surfaces 41 and 45 define a typical electrode area. On the bottom surface 45 of substrate 20, the interconnection circuit 24 is deposited by conventional photoresist etching techniques. Holes 48 are filled with electrode conductor material, such as pyrolytic carbon, to provide electrical connection between surfaces 41 and 45 of substrate 20. The deposition of the pyrolytic carbon is conventionally effected by an appropriate masking technique.

Interconnection circuit 24, containing connectors 25 for connecting electrodes 22 in each sensor site 14, is formed over surface 45 of substrate 20. A thin coat 46 of epoxy is layed over surface 45 to protect the interconnection circuit 24.

On the upper surface 41, a layer 50 of thermoplastic material is then deposited to form the necessary well-shaped sensor sites 14, as defined by surfaces 16, 40, 42 and 43. In some cases, (FIG. 7b) sensor construction requires photoresist layers 44 prior to the thermoplastic well formation.

Next, the chemical layers are formed at each sensor site 14 by depositing layers 51, 52, 53, 54, etc. After layers 51, 52, 53, 54, etc. have been deposited, the chip 10, with the exception of the contact area 18 defined by borders 60 (FIGS. 1a and 2), is coated with an epoxy or thermoplastic layer 12b defining a support tray 11. A protective semi-permeable barrier layer 12c is then deposited over the blood contact area 18. If desired, the entire chip 10 and tray 11 may be overlayed with the aforementioned tear-away impermeable layer 12a of FIG. 1, or the encapsulation envelope 12b of FIG. 1a.

Now referring to FIGS. 5, 6, and 7a through 7d, a typical row of sensors 14a, 14b, 14c, and 14d are respectively illustrated to describe four different basic sensor electro-chemistries. Each of the sensors 14a, 14b, 14c, and 14d have electro-chemistries which will apply to the other similar sensors upon chip 10 and with respect to other contemplated analytes being assayed.

The sensor 14a shows a sensor construction for measuring glucose (GLU) in the blood sample. The glucose in the blood will permeate and filter through the barrier layer 12c and a further cellulose filtering layer 70, respectively, and then diffuse into a polymer or gel layer 71a containing the enzyme glucose oxidase. Hydrogen peroxide is produced in layer 71a from the enzyme-catalyzed oxidation of glucose within the polymer layer. The hydrogen peroxide diffuses through layer 71a to the surface 22a of electrode 72a. The concentration of the hydrogen peroxide is monitored by measuring the anodic current produced at electrodes 72a by the electro-oxidation of hydrogen peroxide at +0.7 volts vs. silver/silver chloride reference electrode as applied at electrodes 72b vs. 72c and 72a vs. 72c. Alternatively, the total anodic charge may be measured. Layer 71b is similar to layer 71a, but does not contain the enzyme glucose oxidase. Therefore, as glucose diffuses through layers 12c and 70 into layer 71b, no reaction will be monitored at electrode surface 22b of electrode 72b. This electrode 72b acts as an error correcting electrode. The signal from electrode surface 22b will be subtracted from the signal of electrode surface 22a by differential measurement to eliminate other oxidizable interferences in the blood sample.

The reference electrode 72c extends in an annular fashion (shown only in cross-section here) about electrodes 72a and 72b. Thus, the surface 22c of electrode 72c is made much larger in area than electrode surfaces 22a and 22b, in order to maintain voltage stability during measurement (during current flow). Electrode 72c supports the current flow of sensor 14a. The formal potential of the electrode 72c is maintained by annular layer 71c (also only shown here in cross-section), which comprises a Cl$^-$ containing polymer or gel (Ag/AgCl with Cl$^-$). The reference electrode 72c is the Ag/AgCl electrode couple. The respective electrodes 72a and 72b are composed of carbon and are connected electrically to respective wires 25. The annular reference electrode 72c may contain carbon or Ag.

Figure 7B:
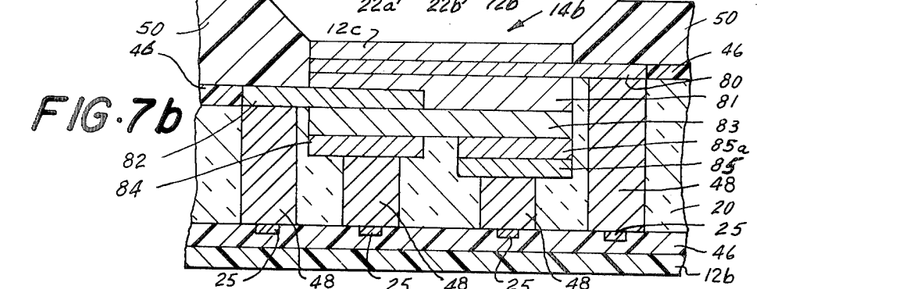
FIG. 7b depicts a typical kinetic measuring cell for LDH measurement.
Figure 8:
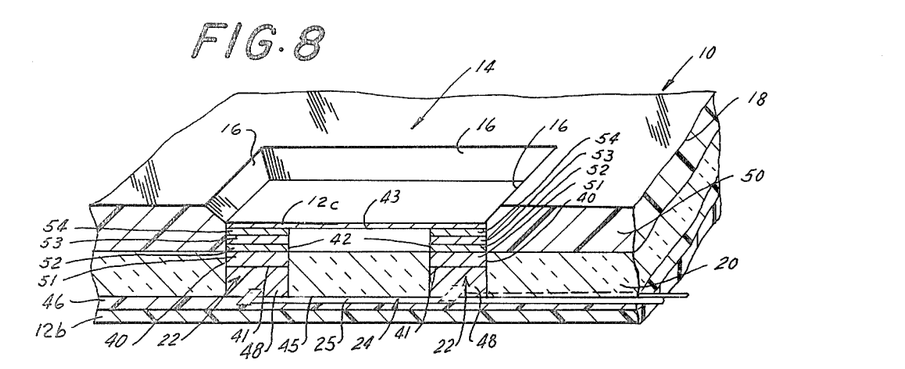
FIG. 8 is an enlarged cut-away perspective view of a typical sensor assembly of FIG. 4.
Figure 8A:
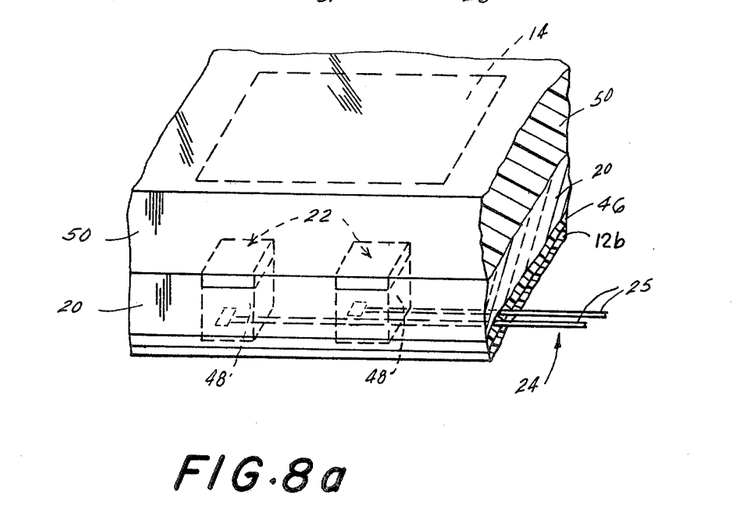
FIG. 8a is a perspective partial view of the electrode-substrate-circuit construction of FIG. 8.

Sensor 14b of FIG. 7b is designed to measure LDH in the blood sample. The chemistries used for determining LDH, as well as other enzyme analytes in blood requires that a kinetic rate be measured. In the past, kinetic rate measurements of this type always have required the measurement of time dependent parameters. Therefore, two or more readings in time or a continuous monitoring was required to obtain kinetic rate measurement. Sensor 14b, however, is constructed in a new way in order to make use of a new method of measuring kinetic rate. The new method will provide a virtually immediate enzyme activity reading. Only one reading is required, and the electro-chemical sensor is not subject to electrode surface effects that will alter the calibration, nor to prior experienced changes in the electrochemical nature of the gel composition resulting from current flow during the measurement. Furthermore, the enzyme reaction does not occur until actuated by a new type of current generating electrode of the sensor, as will be explained hereinafter. The inventive sensor 14b is a more accurate, reliable, and convenient device for determining enzyme analytes requiring a kinetic rate measurement.

The new method of the invention features controlling the concentration of the reactants in the following LDH related enzyme reaction for a given time interval:

When the reactants are controlled, a steady state condition will apply for this extended period of time. During this steady state condition, a single measurement of the kinetic rate of the enzyme reaction will determine the activity of the LDH enzyme. Obviously, only a single measurement need be made because there will be no change in kinetic rate with time (steady state). The formation of the NAD+ is kept at a very high level to maintain maximum rate and linearity of response. A pyruvate trap is provided to force the reaction to the right and prevent a back reaction from influencing the monitored forward reaction. This is accomplished by impregnating the enzyme reaction layer with a semicarbazide, which will react with the pyruvate product. This method of kinetic rate measurement may also be used in other media besides thin film. It can be used either in a batch sampling analysis or in a continuous flow analysis, as long as the mass transport of reactants, i.e., flow rates and mixing, is also controlled.

The LDH of the blood sample initially permeates the barrier layer 12c and is then diffused through a second barrier layer 80 of an electrically conductive material such as sintered titanium oxide, tin oxide or porous graphite. The barrier layer 80 also serves as the counter or auxiliary electrode of the sensor, and is connected to a wire 25 of circuit 24 by means of a current conductor 48, as aforementioned. The LDH next permeates to a gel layer 81 containing the enzyme substrate (such as lactic acid) and a coenzyme NADH. The NADH in this layer is electrochemically converted to NAD+ by means of a generating electrode 82, which is carbon deposited within gel layer 81, as shown. Layer 81 also contains a semicarbazide for trapping the pyruvate product of the reaction. The electrode 82 receives predetermined constant current from the analyzing device 30 via a wire 25 and vertical current conductor 48. The rate of formation of NAD+ will be controlled due to the predetermined constant current being fed to the generating electrode 82.

This generating rate is measurable by the monitoring electrode 84, which is positioned below the reactant generating electrode 82. However, as the LDH of the sample diffuses through layer 81 into polymer layer 83, the NAD+ which is being generated at electrode 82 will be consumed by the enzyme catalyzed reaction with the lactate substrate. The electrode 84 will now sense the rate at which the NAD+ is being reconverted to NADH. Therefore, the monitoring electrode 84 will sense the altered NAD+ generating rate. The altered current flow from that of the initial NAD+ generating rate is directly proportional to the activity of LDH in the sample. Polymer layer 83 also acts as a medium for the reference electrode of the sensor 14b. All the electrodes 80, 82, 83, and 84, respectively, are electrically connected to respective wires 25 via carbon conductors 48. The monitoring electrode 84 will provide the analyzer 30 with an almost immediate current or charge that will be a single measurement or reading of the kinetic rate of the reaction. Reference electrode 85 comprises a film of carbon covered by a polymer layer 85a which contains quinone/hydroquinone to define a stable redox potential.

If the LDH or other enzyme analyte were measured the old way by taking several readings with respect to time, sensor 14b would be constructed more like sensor 14a. The new method of measurement, as applied to thin film integration, however, does not require a difficult structure to fabricate. Yet, it provides an enormous advantage of obtaining a reading in only a few seconds required for steady state conditions to be achieved. This new method and sensor construction makes the integrated circuit approach to blood analysis more viable than any device previously contemplated since many enzymes in the blood can be easily and quickly analyzed by this approach. This is so, because this method greatly simplifies the electronics needed to determine the kinetic rate (no time base required), and it is more accurate and reliable due to the shortened period of response required to accomplish this measurement. Also, because the reagent is generated at will, the device has improved shelf-life and over-all stability, i.e., the reaction starts only when the system is ready to accept data. As a result, it doesn't matter whether a portion of the NADH in layer 81 degrades during storage because the generation is controlled.

Figure 7C:
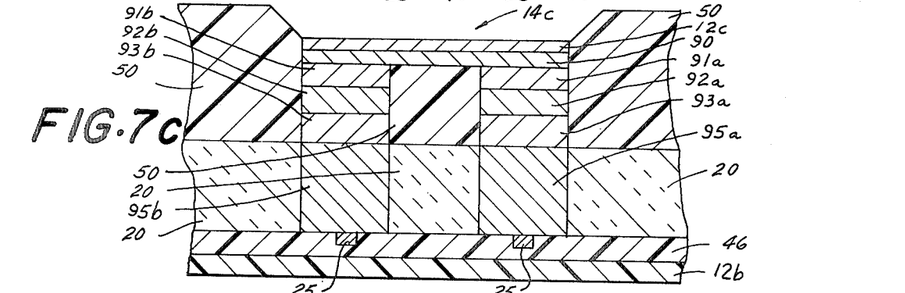
FIG. 7c illustrates a typical ion-selective cell with immobilized enzyme in a gel layer for potassium ion measurement.

Sensor 14c illustrates a sensor construction required for determining the K+ analyte in blood. After the K+ filters through the initial barrier layer 12, it diffuses into a layer 90 of cellulose which is a permeable secondary and optional barrier/filter medium. The sensor 14c is structured as a twin electrode sensor comprised of two identical potassium sensing electrodes. The right-hand electrode 95a functions as a reference electrode because its potassium concentration is fixed by the gel layer 91a and, hence, provides a fixed half-cell potential for the left-hand electrode 95b.

Layer 95a together with layer 91b provides the means for sensitivity calibration of sensor 14c. Layers 91a and 91b each have a predetermined concentration of K+, but one which sets up a differential voltage signal between the two electrodes, e.g., layer 91a could have 5.0 mEq./L of K+, whereas layer 91b could only have 1.0 mEq./L of K+ and ideally the resulting voltage between them should be 42 mV, but for practical purposes the voltage will vary depending primarily on fabrication irregularities. Hence, the twin electrodes 95a and 95b provide a differential measurement which allows actual sensitivity calibration prior to sample measurement and at the same time will nullify any drift and offsets in the measurement.

The cellulose layer 90 filters the blood sample to allow only K+ ion to filter to the lower layers.

Layers 12c and 90 are designed to allow diffusion of ions in the sample primarily into layer 91b where the change in voltage of electrode 95b yields the additional potassium introduced by the sample. Alternatively, the differences in concentrations in layers 91a and 91b can be made so large that diffusion of sample potassium into layer 91b will not constitute a significant error. For example, if layer 91a contains 0.1 mEq./L of K+ and layer 91b contains 100 mEq./L of K+ then a 5 mEq./L sample would result in voltage changes of 102 mV and 1.3 mV, respectively. If uncompensated, the 1.3 mV voltage change of electrode 95b would only constitute an assay error of 0.2 mEq./L. However, regardless of the concentrations of K+ in layers 91a and 91b, an algorithm can be written to take into account the signal changes, however minute, in both electrodes 95a and 95b. From a practical standpoint, however, the reference side of the sensor should not change significantly in voltage relative to the other sample sensing side.

Layer 93a directly above the reference electrode 95a contains ferro/ferric-cyanide to form a stable redox couple for electrode 95a and also a fixed K+ concentration to maintain a stable interfacial potential between layers 93a and 92a. Layer 92a above layer 93a is polyvinyl chloride impregnated with a neutral ion carrier valinomycin, which is selective to potassium.

Layers 92b and 93b, respectively, are identical layers to their counterpart layers, 92a and 93a, with the exception of the reagents contained therein.

The calibrating layers 91a and 91b, respectively, may be maintained at a given or predetermined distance above the electrodes. Also, their thickness or size may be carefully controlled in manufacture. This will insure predetermined electrical characteristics such as capacitance and impedance for the sensor.

Figure 7D:
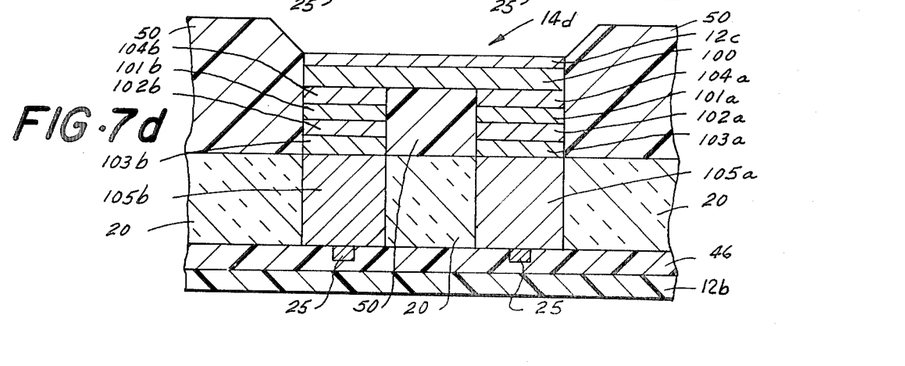
FIG. 7d shows a typical potential measuring cell for BUN measurement.

Sensor 14d depicts a construction necessary for the assay of Blood Urea Nitrogen (BUN).

The urea assay is accomplished by the sensing of the ammonium ion $NH_4+$. The urea in the blood permeates the barrier layer 12c and the cellulose barrier layer 100. Layer 101a comprises a polymer containing an immobilized enzyme such as urease. Within this layer 101a, the urea of the sample is catalytically hydrolyzed to ammonium bicarbonate by urease. The $NH_4$ diffuses into the next layer 102a which is a polyvinyl chloride containing an antibiotic such as nonactin as the neutral ion carrier. The $NH_4+$ is at the interface layers 101a and 102a. The next layer 103a is a gel containing the electrode couple $Fe(CN)_6^{3-}/Fe(CN)_6^{4-}$ introduced as ammonium salts. The carbon electrode 105a lies below layer 103a. Electrode 105a in contact with layer 103a serves as the inner reference electrode for the $NH_4+$ sensor 14d. The interfacial potential at the layers 102a/103a is fixed by the ammonium ferrocyanide salt concentration, and only the interfacial potential of layers 101a/102a will vary with sample urea concentration.

Electrode 105b serves to subtract interferences by measuring the differential of the potential. Layers 101b, 102b, and 103b, respectively, are similar to layers 101a, 102a, and 103a, except that layer 101b does not contain urease as its counterpart layer 101a.

Layers 104a and 104b of the sensor are impregnated with a known or predetermined amount of $NH_4+$ to internally calibrate the sensor sensitivity and compensate for drifts. These layers, similar to the calibration layers in sensor 14c, contain high and low levels of the measured species ($NH_4+$) or alternately the analyte itself (urea).

These predetermined impregnated layers in sensors 14c and 14d which provide self-calibration, not only assure built-in reliability and accuracy, but relax manufacturing tolerances. Thus, sensor fabrication is greatly facilitated by the built-in calibration.

As aforementioned, many more tests will be performed by the other sensors in the chip array, but all the other sensors, despite their different chemistries, will have the same structure as one of these four sensors (14a, 14b, 14c, and 14d). The following Table I is a list of intended measureable analytes, and their corresponding sensor structures, i.e., whether they resemble sensor construction for sensors 14a, 14b, 14c, or 14d, respectively. The immobilized reagents for the various analytes under assay are also given.

TABLE I

| Analyte | Enzyme/ Substrate | Measurement (*) | Type of Sensor | Species Monitored |
|---|---|---|---|---|
| I. Electrolytes | | | | |
| Sodium ($Na^+$) | | P | 14c | |
| Potassium ($K^+$) | | P | 14c | |
| Lithium ($Li^+$) | | A | 14a | |
| Calcium ($Ca^{2+}$) | | P | 14c | |
| Chloride ($Cl^-$) | | P | 14c | |
| $CO_2$ (tot.) ($HCO_3^-$) | | P | 14c | |
| Ammonia ($NH_3$) | | P | 14c | |
| II. Gases | | | | |
| Oxygen ($pO_2$) | | P | 14a | |
| Carbon Dioxide ($pCO_2$) | | P | 14c | |
| pH | | P | 14c | |
| Hemoglobin | Catalyst/Redox Mediator | A | 14a | |
| III. Substrates | | | | |
| Glucose | Glucose Oxidase | A | 14a | $H_2O_2, O_2$ |
| Urea (BUN) | Urease | P | 14d | $NH_3(g), NH_4^+$ |
| Creatinine | Creatininase | P | 14d | $NH_3(g), NH_4^+$ |

TABLE I-continued

| Analyte | Enzyme/ Substrate | Measurement (*) | Type of Sensor | Species Monitored |
|---|---|---|---|---|
| Uric Acid | Uricase | A | 14a | $H_2O_2$, direct |
| Cholesterol | Cholesterol Oxidase (Cholesterol Hydrolase) | A | 14a | $H_2O_2$, $O_2$ |
| Lactic Acid | LDH | A | 14a | $NaDH^+/NADH$ |
| Pyruvic | LDH | A | 14a | $NAD^+/NADH$ |
| Inorganic Phosphorus | Alk. Phosphatase | A | 14a | $O_2, H_2O_2$ |
| Total Proteins | — | P | 14d | $Ag^+$ |
| Ascorbic Acid | — | A | 14a | direct |
| Bilirubin | — | A | 14a | direct |
| Triglycerides | Lipase | P | 14d | pH |
| Pheylalanine | Decarboxylase | P | 14d | $pCO_2$ |
| Tyrosine | Decarboxylase | P | 14d | $pCO_2$ |
| IV. Enzymes | | | | |
| Lactic Dehydrogenase (LDH) | Lactate/ Pyruvate | A | 14b | $NAD^+/NADH$ |
| Lipase | Triglycerides | A | 14b | pH |
| Amylase | | A | 14a | $H_2O_2$ |
| Choline Esterase | Acetylcholine | P | 14d | pH |
| GOT | MDH | A | 14b | $NAD^+/NADH$ |
| GPT | LDH | A | 14b | $NAD^+/NADH$ |
| CPK | Hexokinase G-6-PD | A | 14b | $NADP^+/NADPH$ |
| Alk. Phos. | (Phenylphosphate and Plyphenyl-Oxidase | A | 14a | $H_2O_2$ |
| Acid Phos. | (Phenylphosphate and Plyphenyl-Oxidase) | A | 14a | $H_2O_2$ |

Figures 11, 12:
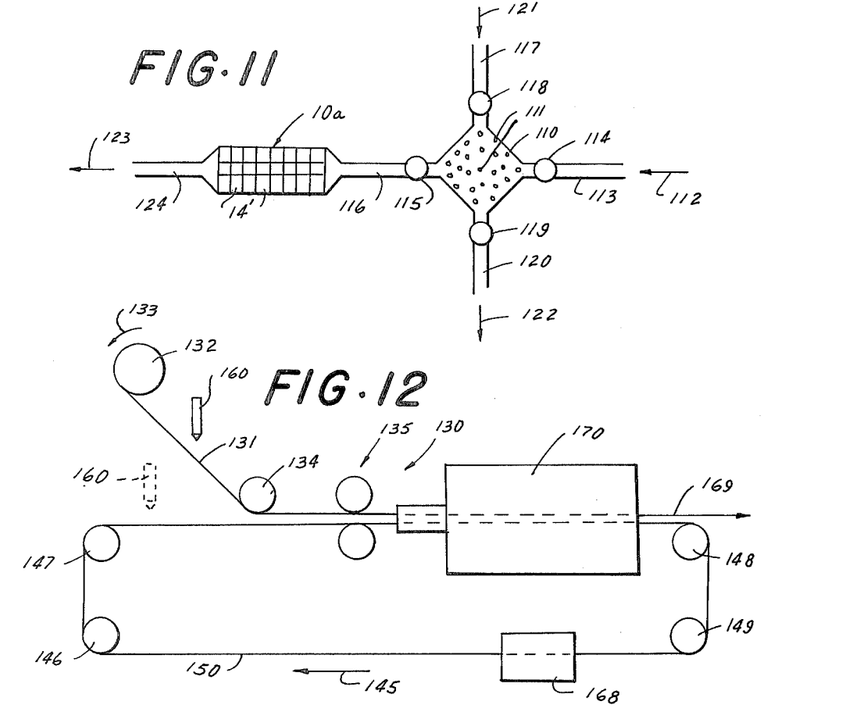
FIG. 11 is a schematic diagram of a continuous flow system for analyzing a fluid using a modified chip as that illustrated in FIG. 4.
FIG. 12 is a schematic diagram of a continuous system of using thin films to form a plurality of fluid analyzing sensors.

*P = Potentiometric Electrode Measurement
A = Ampermetric or Voltommetric Measurement Referring to FIG. 11, another embodiment of the integrated chip approach to analyte testing is shown. Chip 10 is replaced by a new thin film sensor matrix 10a, which comprises sensors 14' having just the electrode structures, redox and calibration layers upon a common substrate. The enzyme layers are absent. Instead, the necessary enzymes for each sensor reaction are contained in a reaction cell or chamber 110. The enzymes are supported upon polymer beads 111 or hollow fibers, etc. The chamber 110 may also be constructed to contain a porous polymer for this purpose.

The sample under analysis is introduced into chamber 110 (arrow 112) via conduit 113 and valve 114. The analytes of the sample each respectively react with their specific enzyme, and are then discharged via valve 115 and conduit 116 to sensor matrix 10a.

Each sensor 14' of matrix 10a will sense a particular analyte-enzyme reaction as before, i.e., some sensors 14' will measure current, some potential, and some kinetic rate differentials.

After the sensors 14' have accomplished their analyses of the sample, the reaction cell 110 and the matrix 10a are washed clean. A first wash liquid is introduced (arrow 121) into conduit 117 and enters chamber 110 via valve 118. The wash is allowed to soak through beads 111 and is discharged (arrow 122) from the chamber 110 via valve 119 and conduit 120. A second wash liquid is then introduced to chamber 110 via conduit 113 and valve 114. The second wash is forced through chamber 110 and is continuously flushed through valve 115 and conduit 115 to matrix 10a. The second wash will flow past matrix 10a cleaning sensors 14', and then discharges (arrow 123) from the matrix 10a via conduit 124.

Naturally, the valves 114, 115, 118 and 119, are respectively opened and closed in proper sequence to accomplish the various sample and wash cycles.

After the second wash, the next sample is introduced into the reaction cell, and the same procedure is followed.

Figure 13:
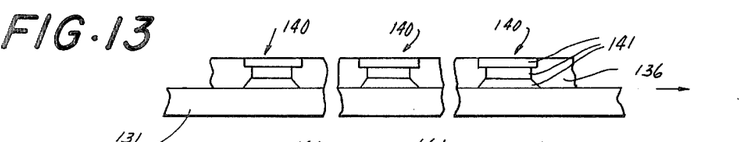
FIG. 13 is an enlarged cross-sectional view of the films depicted in FIG. 12.
Figure 14:
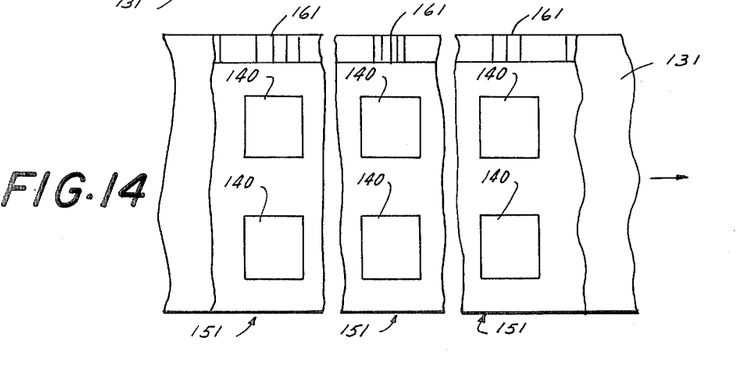
FIG. 14 is an enlarged plan view of the film shown in FIG. 13.

FIGS. 12-14 illustrate still another embodiment of the thin film integrated circuit approach of this invention. FIG. 12 shows an automatic continuous analyzing system 130. A first continuous endless web 131 is stored and dispensed (arrow 133) from reel 132. The web 131 travels past tensioning roller 134 toward a pair of pressure rollers 135. The first endless web 131 comprises discrete partial sensors 140 disposed within a common substrate layer 136 deposited on belt 131 as depicted in FIG. 13. Each partial sensor 140 is individually comprised of the necessary gel and polymer layers 141 common to the respective sensors 14a, 14b, 14c, etc., of chip 10. The partial sensors 140 are each sequentially disposed upon the common substrate 136, but rows 151 of various numbers of partial sensors 140 can be disposed transversely across web 131 as illustrated in FIG. 14.

A second continuous web 150 (FIG. 12) is advanced (arrow 145) about a frame of rollers 146, 147, 148, and 149, as shown. The second web 150 comprises the electrode structures (not shown) for the corresponding partial sensors 140 of belt 131. When the belts 131 and 150 are advanced and married by pressure rollers 135, a series of completed sensors are formed with structures similar to the sensors 14a, 14b, 14c, etc.

Prior to the completion of the full sensor structures by the pressure rollers 135, either web 131 or web 150 passes a sample dispenser 160. The dispenser 160 is preferably placed over the web 131 (solid lines) instead of web 150 (dotted lines). A drop of sample liquid is dispensed to each partial sensor 140, and permeates the various respective layers 141.

When the electrodes of the web 150 merge with the sample impregnated enzyme layered sensor medium 140, analytes of the sample will already be reacted. The various signals and information will be conveyed through the electrodes to an analyzer 170 as both the merged webs 131 and 150 pass therethrough, as illustrated.

At the rear of the analyzer 170, the spent web 131 is discarded (arrow 169). The electrode web 150, however, may be passed by a wash or reconditioning station 168, and can be recycled.

The web 131 may contain an identifying code 161 opposite each particular sensor or sensors 140. This code 161 will be read by the analyzer 170 to properly record the analyzed data.

Figure 9:
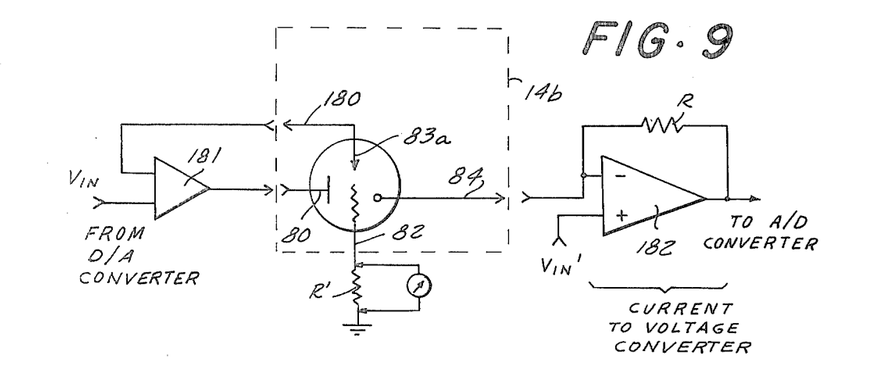
FIG. 9 is a schematic electrical diagram of a conditioning circuit for the output of the enzyme sensor shown in FIG. 7b.

Referring to FIG. 9, a testing circuit for the enzyme sensor 14b of FIG. 7b is illustrated. The auxiliary electrode 80 and the reference electrode 83a will form part of a potential stabilizing feedback loop 180 for controlling the voltage between these electrodes. The loop 180 comprises an amplifier 181, which receives an input voltage $V_{in}$. The applied voltage is sensed at the generating electrode 82. Amplifier 181 supplies the current to the generating electrode 82 via the auxiliary or counter electrode 80.

The sensing electrode 84 is voltage biased at amplifier 182 by $V_{in}$, and the current is monitored by this amplifier.

The voltage $V_s$ sensed from the generating electrode is given as:

$$V_s = V_{in} - V_{Ref}$$

The voltage $V_a$ applied to the sensing electrode 84 is given as:

$$V_s = V_{in} + V_{in}' - V_{Ref}$$

Figure 3:
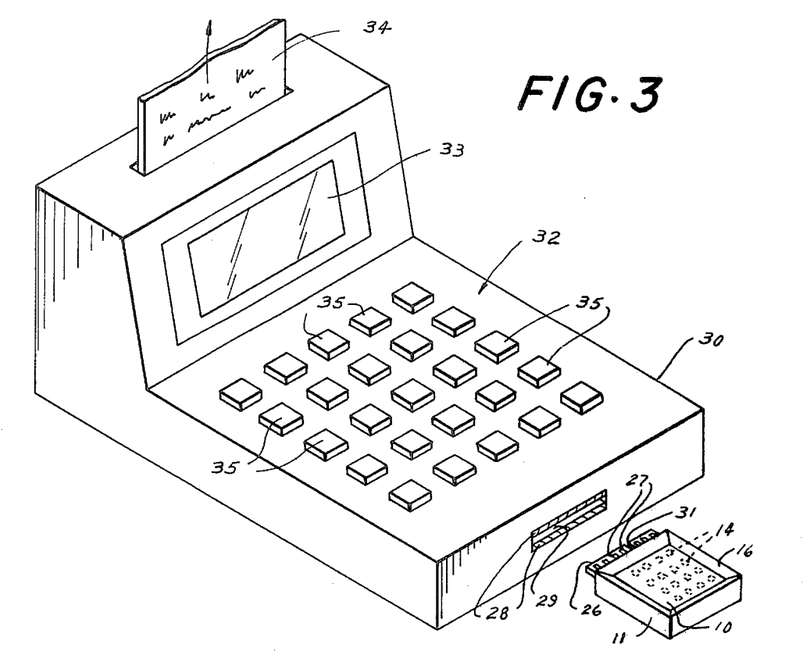
FIG. 3 is a perspective view of a hand-held analyzer or computer for receipt of the substrate supported chip of FIG. 2, and for analysis of the fluid deposited upon the chip.
Figure 3A:
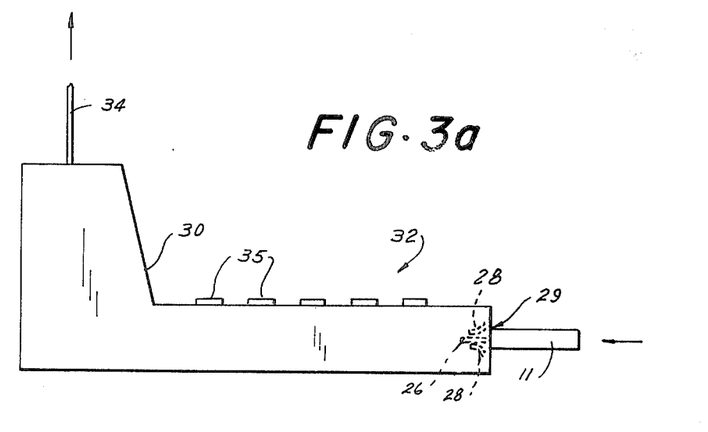
FIG. 3a is a side view of FIG. 3.
Figure 10:
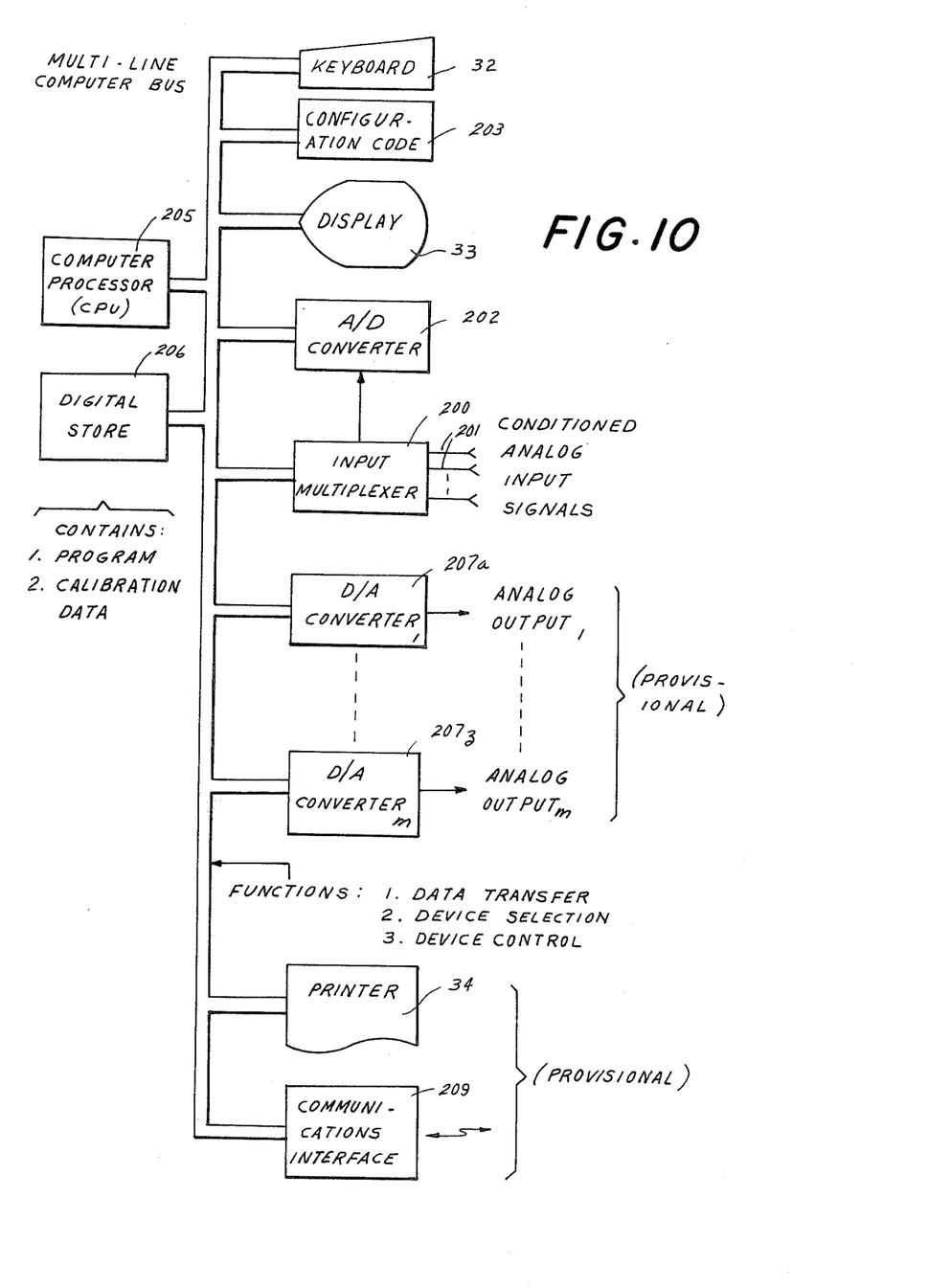
Figure 10A:
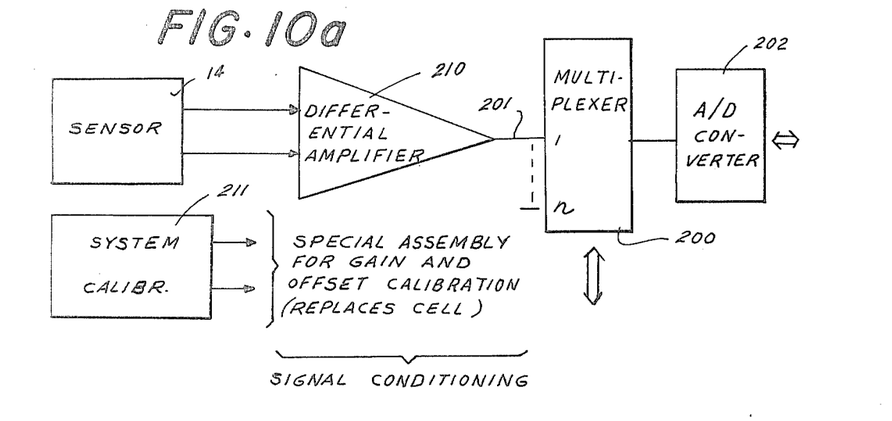
FIG. 10a is a more detailed schematic diagram for a portion of the circuit of FIG. 10.

Referring to FIGS. 10 and 10a, a schematic of the computer configuration for analyzer 30 of FIGS. 3 and 3a is illustrated.

The computer is under the control of the central processor (CPU) 205, which derives its instructions from a stored program in memory 206, which also contains calibration data for adjusting the processed signals, and stores data in working and permanent storage. The processor 205 does all the arithmetic calculations and processing of the sensor signals. The sensor signals are fed from chip 10 into the analyzer 30 via connectors 28 (FIG. 3). After an initial conditioning of the signals 201, they are multiplexed by multiplexer 200, and then converted to digital form by the analog-to-digital converter 202. When a particular key 35 (FIG. 3) of keyboard 32 is depressed, the key calls for a specific analyte analysis or other appropriate programmed sequence via the process coder 203. The appropriate signal from chip 10 is then processed by the CPU. The processed signal may then be displayed by display 33 and/or a hard copy made by the printer 34. All the signals are properly called up, processed and read under the guidance of the process coder 203. Where desired, an optional set of digital-to-analog converters 207a–207z will provide an analog input for other peripheral devices. Also, a communication interface 209 can be provided for talking to another computer device, such as a master computer at a data center.

FIG. 10a depicts the signal conditioning for signals from a typical sensor 14. The signals from sensor 14 are amplified, biased, and calibrated via the differential amplifier 210 and calibrator controls 211. Then the output 201 from the amplifier 210 is fed to one of the inputs 1 through n of multiplexer 200. The multiplexed signals are fed to the analog/digital converter 202, as aforementioned.

The various techniques for constructing the integrated circuit chip are well known to the practitioners of the electrical arts, but a better understanding of the techniques expressed herein may be obtained with reference to: L. I. Maissel and R. Glang; Handbook of Thin Film Technology; McGraw-Hill Book Co.; Copyright 1970.

Having described the invention, what is desired to be protected by Letters Patent is presented by the following appended claims.

What is claimed is:

1. An article of manufacture used for analyzing a multiplicity of analytes in a fluid sample, said article comprising an array of discrete, electrically isolated electrochemical sensors supported on a common substrate for analyzing different ones of said analytes, at least one of said sensors in said array having a built in calibrating means including means to establish a differential concentration of an analyte within said one sensor during measurement comprising, a first electrode layer containing a given concentration of the analyte being measured, and a second electrode layer containing a given but different concentration of the analyte being measured, and electrical means to provide access to each of said sensors.

2. The article of manufacture of claim 1, wherein said electrical means comprises electrical conductors supported upon said substrate to provide access to said discrete sensors, said conductors extending to a periphery of said substrate to define a plug-in type connector.

3. The article of manufacture of claim 2, wherein said electrical connectors comprise printed connectors deposited upon a common substrate.

4. The article of manufacture of claim 3, wherein selected ones of said sensors comprise printed electrodes deposited upon said substrate in electrical continuity with respective ones of said printed connectors.

5. The article of manufacture of claim 3, wherein said printed connectors are adapted to be received in a snap-in receptacle of an analyzing means responsive to at least selected ones of said sensors.

* * * * *